(12) United States Patent
Patnaik et al.

(10) Patent No.: US 10,524,807 B2
(45) Date of Patent: Jan. 7, 2020

(54) ACCESSORY FOR CONDUCTING PATELLA SURGERY

(71) Applicants: University of Cape Town, Rondebosch (ZA); Sarthak Patnaik, Keonjhar (IN)

(72) Inventors: Sarthak Patnaik, Keonjhar (IN); Sudesh Sivarasu, Kenilworth (IN)

(73) Assignees: Sarthak Patnaik, Odisha (IN); University of Cape Town, Cape Town (ZA)

( * ) Notice: Subject to any disclaimer, the term of this patent is extended or adjusted under 35 U.S.C. 154(b) by 171 days.

(21) Appl. No.: 15/741,223

(22) PCT Filed: Jul. 1, 2016

(86) PCT No.: PCT/IB2016/053967
§ 371 (c)(1),
(2) Date: Dec. 29, 2017

(87) PCT Pub. No.: WO2017/002085
PCT Pub. Date: Jan. 5, 2017

(65) Prior Publication Data
US 2018/0185039 A1     Jul. 5, 2018

(30) Foreign Application Priority Data

Jul. 2, 2015 (GB) .................................. 1511597.5

(51) Int. Cl.
*A61B 17/17* (2006.01)
*A61B 90/00* (2016.01)
*A61B 17/00* (2006.01)

(52) U.S. Cl.
CPC ...... *A61B 17/1767* (2013.01); *A61B 17/1714* (2013.01); *A61B 2017/0023* (2013.01);
(Continued)

(58) Field of Classification Search
CPC .................... A61B 17/1767; A61B 17/1714
See application file for complete search history.

(56) References Cited

U.S. PATENT DOCUMENTS

| | | | | |
|---|---|---|---|---|
| 4,633,862 A | * | 1/1987 | Petersen | A61B 17/158 606/211 |
| 5,431,651 A | * | 7/1995 | Goble | A61B 17/1714 606/102 |

(Continued)

FOREIGN PATENT DOCUMENTS

| | | |
|---|---|---|
| EP | 1618849 A1 | 1/2006 |
| JP | 2001 070311 A | 3/2001 |

(Continued)

*Primary Examiner* — Christian A Sevilla
(74) *Attorney, Agent, or Firm* — Workman Nydegger

(57) ABSTRACT

An accessory is provided for use in the conduct of patella reconstruction surgery. The accessory comprises an elongate datum limb for abutment in use with the superior pole of a patella preferably through the skin. An elongate guide limb for abutment by a side edge of a patella extends transversely relative to the datum limb has guide holes passing through it or an insert carried by it at positions selected to direct a drill or other surgical tool at an edge of the patella to enable holes or tunnels to be formed in the patella at required positions for the attachment or reception of reconstructive ligaments to the patella. Attachment limbs enable the accessory to be secured in an operative position relative to a patella. There may be slots formed by anchor bars integral with the guide limb and attachment limb to strap the accessory to a patient's knee.

14 Claims, 6 Drawing Sheets

(52) U.S. Cl.
CPC ............... *A61B 2017/00991* (2013.01); *A61B 2090/062* (2016.02); *A61B 2090/067* (2016.02); *A61B 2090/3983* (2016.02)

(56) References Cited

U.S. PATENT DOCUMENTS

| | | | |
|---|---|---|---|
| 5,667,512 A | 9/1997 | Johnson | |
| 2004/0254585 A1* | 12/2004 | Whittaker | A61B 17/1714 606/104 |
| 2011/0166574 A1 | 7/2011 | Hsu | |
| 2013/0079788 A1* | 3/2013 | Spencer Jones | A61B 17/1767 606/96 |

FOREIGN PATENT DOCUMENTS

| | | |
|---|---|---|
| JP | 2002 102236 A | 4/2002 |
| JP | 2009 011517 A | 1/2009 |
| WO | 00/35359 A1 | 6/2000 |
| WO | 2010/019384 A1 | 2/2010 |

* cited by examiner

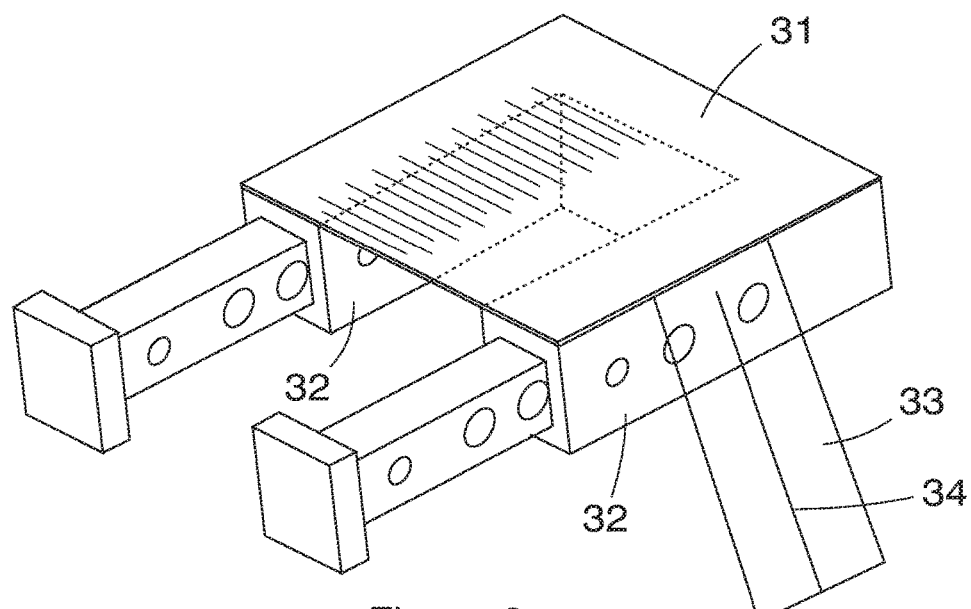
Figure 9
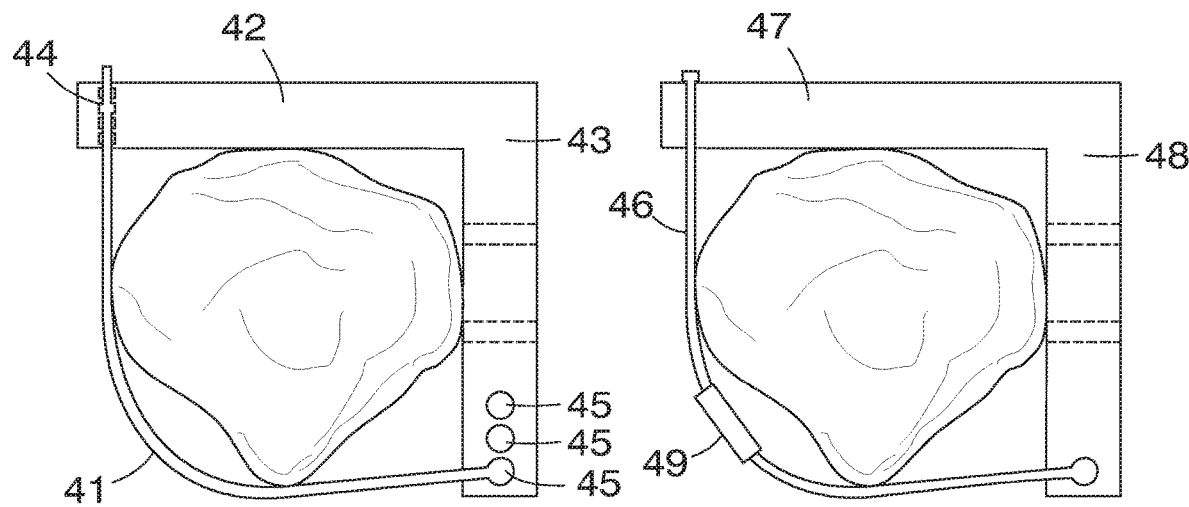
Figure 10
Figure 11

ACCESSORY FOR CONDUCTING PATELLA SURGERY

CROSS-REFERENCE TO RELATED APPLICATIONS

The present invention is a 35 U.S.C. § 371 U.S. National Stage Application corresponding to PCT Application No. PCT/IB2016/053967, filed on Jul. 1, 2016, which claims priority to U.K. Application No. 1511597.5, filed Jul. 2, 2015. The entire content of each of the aforementioned patent applications is incorporated herein by reference.

FIELD OF THE INVENTION

This invention relates to an accessory for conducting patella surgery and, in particular, an accessory that is aimed at assisting a surgeon in forming attachment holes or tunnels in the patella during medial patella femoral ligament reconstruction.

BACKGROUND TO THE INVENTION

Patella dislocation is one of the most common pathologies of the knee joint. The medial patella femoral ligament plays a pivotal role in the avoidance of patella-femoral instability. Rupturing of the medial patella femoral ligament is the main pathological consequence of patellar dislocation. All acute dislocations cause some degree of macroscopic medial patella femoral ligament damage and studies have shown that lateral dislocation invariably results in at least some damage to the medial patella femoral ligament. About 44% of non-conservative treated patients go on to suffer re-dislocation along with painful symptoms and chronic instability.

Medial patella femoral ligament reconstruction surgeries prevent further dislocation of patella by adopting one of the surgical techniques selected from medial patella femoral ligament reconstruction with a divergent patellar trans 2-tunnel technique; Y graft (fixation of femur first); C graft fixation of patella first (2 incision, first 3 cm longitudinal incision is along the proximal medial border of the patella and another 1 cm above the medial patella femoral ligament insertion); V shaped tunnel in which tunnels are drilled 1.5 cm at the supero medial half of the patella with sufficient distance between the tunnels to avoid fracture; and a docking technique for medial patella femoral ligament reconstruction.

Applicant knows of no special intra-operative method of determining the anatomical location of the patella that can help in identifying the exact medial patella femoral ligament insertion site other than an intra-operative x-ray imaging. Unfortunately, such an x-ray based procedure is accompanied by a high risk of radiation exposure to the patient, the surgeon, any medical assistants as well as other technical staff. The medial patella femoral ligament is the main passive restraint against patella-femoral instability and lateral patellar displacement.

Non-anatomic reconstruction of the medial patella femoral ligament can lead to non-physiologic patella-femoral loads and kinematics. The double bundle technique effectively limits rotation and sliding throughout the range of movement thereby minimizing postoperative instability.

The medial patella femoral ligament may be defined as a thick band like condensation of soft tissues extending from the patella to the medial femur. The average width of patella insertion of medial patella femoral ligament is about 17 mm (a general range of 14 to 20 mm). Average width of the femoral origin on the medial epicondyle is 15.4 mm (a general range of 11 to 20 mm). Average patella height is about 44 mm (a general range of 40 to 47 mm); width is about 34 mm (a general range of 24 to 39 mm) and a thickness of about 22 mm (a general range of 18 to 27 mm).

The inventors perceive that there is scope for the provision of an accessory that obviates, at least to some extent, the need for the use of intra-operative x-rays.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with this invention there is provided an accessory for use in the conduct of patella reconstruction surgery, the accessory comprising an elongate datum limb for abutment in use with the superior pole of a patella optionally through the skin, an elongate guide limb extending transversely relative to the datum limb for abutment with a side edge of a patella, and one or more attachment limbs for enabling the accessory to be secured in an operative position relative to a patella, and guide holes passing transversely through the guide limb at positions selected to direct a drill at an edge region of the patella to enable holes or tunnels to be formed in the patella at least at two required spaced positions for the attachment or reception of reconstructive ligaments to the patella.

Further features of the invention provide for the guide limb to be fixed relative to the datum limb typically at generally right angles to the datum limb; for there to be two spaced parallel guide holes extending at generally right angles to the length of the guide limb so as to direct a drill in a direction at generally right angles to the direction in which an associated quadriceps tendon and patellar tendon extend; for the guide holes to be provided in an insert received in a recess in the guide limb in a selected one of a plurality of different positions along a part of the length of the guide limb; for the insert to have along one edge thereof formations and co-operating with a series of co-operating formations, typically in the form of an integral toothed arrangement extending along one longitudinal edge of the recess; for the insert to have two holes of the same diameter one or both of which optionally receive a removable sleeve for providing an alternative smaller diameter hole through the insert with a preferred interaction between the sleeve and larger diameter hole or insert to inhibit rotation of the sleeve within the larger diameter hole; for an upper hole of the guide holes to be spaced from the superior pole of the patella by a distance that is typically of the order of 8 to 12 mm and commonly about 10 mm with a lower guide hole being spaced from the upper guide hole by a distance in the range of from 10 to 18 mm and typically 12 to 15 mm and especially either 12 or 15 mm depending on the physical configuration of the relevant patella; for the surfaces or edges of the datum limb and guide limb to be provided with recesses or protrusions for cooperation with undulations on the edges of a patella; and for the datum limb and guide limb to mutually support an optionally removable scale panel having guide lines or graduations thereon for assisting a surgeon in estimating a direction at right angles to the guide limb for directing a drill and also for assisting in the assessment of the depth of a hole or tunnel being formed in a patella, the scale panel preferably being transparent.

Additional features of the invention provide for the guide limb to have an integral anchor bar defining with the guide limb itself one, and preferably two longitudinally juxtaposed slots for receiving a strap or straps passing around the anchor bar with an opposite attachment limb having a similar integral bar defining a slot for receiving a belt cooperating with that associated with the guide limb; and for the strap or straps to be made of webbing to which is attached fastening means, preferably in the form of co-operating hook and loop fastener components such as those sold under the trade name VELCRO™/Medical Tapes.

Still further features of the invention provide for the accessory to have an optionally flexible indicator extending from the guide limb in a direction indicating the direction in which reconstructive ligaments should extend in the final reconstruction towards an attachment point in the femur so as to indicate to a surgeon the line in which reconstructive ligaments should extend so as to avoid difficulties consequent on an incorrect direction that can result from erroneous attachment positions. This indicator assists in determining the point between the adductor tubercle and medial epicondyle of the femur to which it is desired to make the attachment. The accessory, which can be fitted to a normal patella of any size, can be adjusted to determine the medial patella femoral ligament attachment site on the patella.

In one variation of the invention the one or more attachment limbs comprises a lateral attachment limb that is spaced from, and extends generally parallel to, the guide limb and a transverse attachment limb that is spaced from, and extends generally parallel to, the datum limb. In such an instance the lateral attachment limb is provided with any anchor bar defining a slot for receiving a belt. Each of the lateral attachment limb and transverse attachment limb are preferably adjustable in positions relative to the datum limb and guide limb so as to form generally rectangular apertures of different sizes in which a particular size of patella can be located. The lateral attachment limb may serve as an alternative guide limb and have guide holes for guiding a drill extending transversely to the patella as envisaged above. The transverse attachment limb may have a downwardly curved shape in at least a central region to accommodate the lowermost apex of a patella.

Many other physical shapes and configurations of the attachment limbs are possible within the scope of the invention.

Thus, in another variation of the invention, a lateral attachment limb may be a mirror image of the guide limb and indeed both of those limbs may be telescopically extensible.

In a further variation of the invention the attachment limbs may be relatively flexible and joined, for example, by a releasable one-way catch, buckle or other tightening mechanism so that they flex to embrace the patella and urge it into contact with the datum limb and the guide limb.

It will be understood that the accessory may be reversed in order to be suitable for use on one side of the body as opposed to the other side of the body in all instances in which an attachment limb does not have guide holes for use from a side of the patella opposite the guide limb.

As a result of the fact that the accessory is used externally of the body skin, it does not need to be made of any particular surgically acceptable materials. It could be made by any appropriate process such as injection moulding, casting, or the like. It could be made of any suitable grade of sterile polyethylene or polyethylene based plastic material, sterile polypropylene or a polypropylene based plastic material, ABS or any other sterile plastic. The accessory can also be made of radiolucent materials such as poly(methyl methacrylate) more commonly known as PERSPEX 6 in Europe and PLEXIGLAS 6 in the USA.

The accessory could alternatively be 3-D printed from appropriate plastic materials and in such an instance the accessory could be made as a custom made accessory for a particular patient with the accessory being 3-D printed for use on that particular patient. However, it is not envisaged that deviations from an average shape and size will be adequate to necessitate individual production unless the physical characteristics of a patient indicate that a custom made accessory would be appropriate. The accessory could then also be disposable.

In this specification the reference to a drill is to be interpreted as meaning any surgical tool capable of creating or processing an attachment formation to which a replacement ligament can be attached.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

In order that the invention may be more fully understood, various embodiments thereof will now be described with reference to the accompanying drawings.

BRIEF DESCRIPTION OF THE DRAWINGS

In the drawings:

FIG. 9 is a three-dimensional illustration of a third embodiment of the invention;

FIG. 10 is a schematic elevation of a fourth embodiment of the invention;

FIG. 11 is a schematic elevation of a fifth embodiment of the invention and,

DETAILED DESCRIPTION WITH REFERENCE TO THE DRAWINGS

Figure 1:
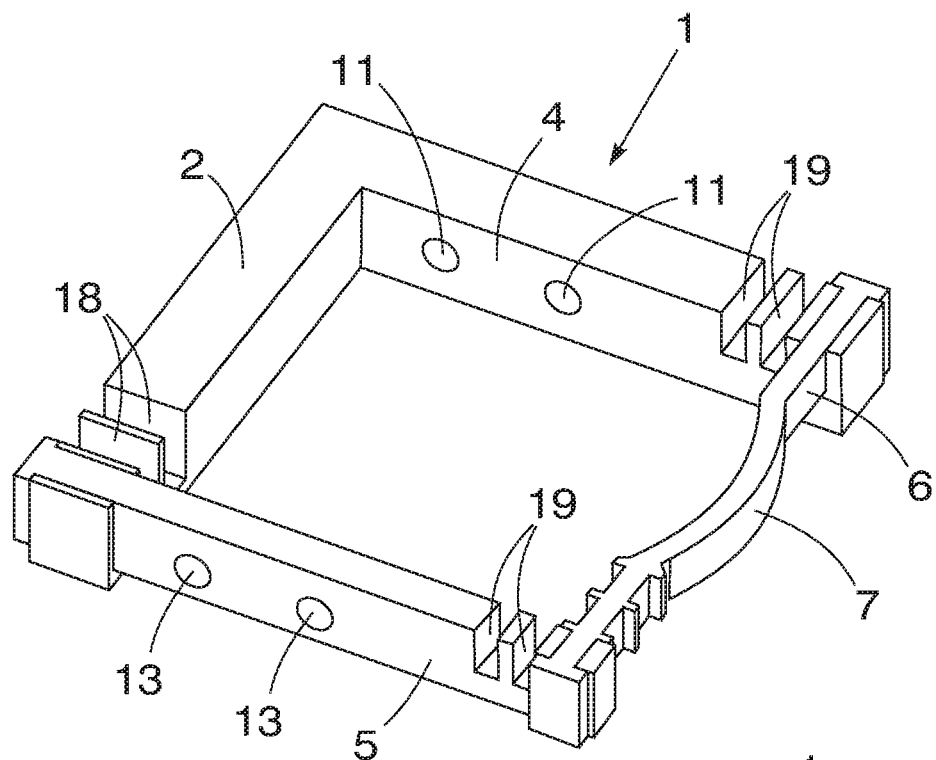
FIG. 1 is a three-dimensional view of one embodiment of the invention without any scale panel attached.
Figure 2:
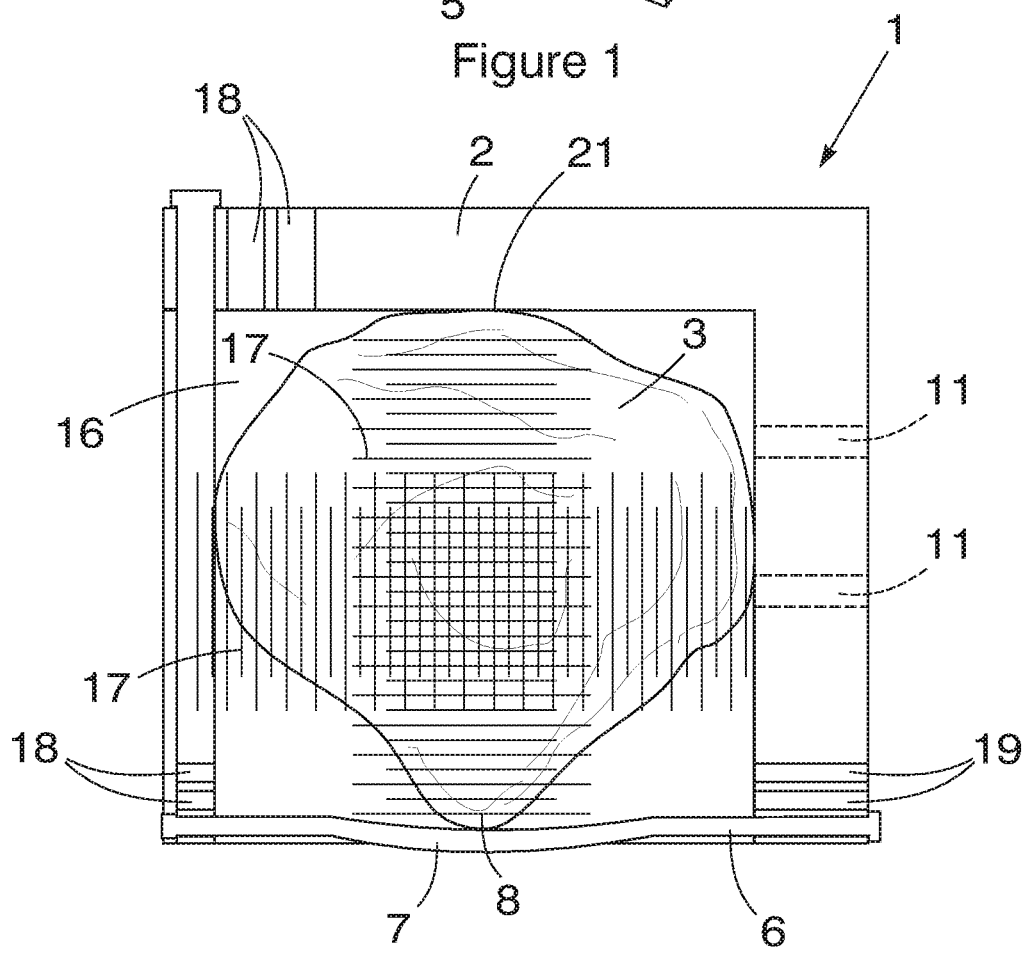
FIG. 2 is a schematic elevation of the same embodiment of the invention with a scale panel attached and installed relative to a patella.

Referring to FIGS. 1 to 4 of the drawings, a basic form of accessory (1) for use in the conduct of patella reconstruction surgery, has an elongate datum limb (2) for abutment in use with the top of a patella (3) through the skin and an elongate guide limb (4) extending at right angles to the datum limb for abutment with a side edge of a patella.

A lateral attachment limb (5) is spaced from, and extends generally parallel to, the guide limb and a transverse attachment limb (6) is spaced from, and extends generally parallel to, the datum limb to form a rectangular aperture. Each of the lateral attachment limb and transverse attachment limb are adjustable in position relative to the datum limb and guide limb so as to form generally rectangular apertures of different sizes in which a particular size of patella can be fitted. The transverse attachment limb may have a downwardly curved shape (7) in a central region to accommodate the lowermost apex (8) of a patella as will be quite apparent from FIG. 6.

A pair of spaced parallel guide holes (11) passes at right angles through the guide limb at positions selected to direct a drill or other surgical tool towards a side edge region of the patella to enable holes or tunnels to be formed in the patella at required positions for the attachment or reception of reconstructive ligaments (12) to the patella (see FIGS. 3 and 4) or for other surgical tools to be guided relative to the guide limb.

In this embodiment of the invention the lateral attachment limb may serve as an alternative guide limb and have a pair of guide holes (13) passing through it for guiding a drill or other surgical tool extending transversely to the patella as envisaged above.

The two spaced parallel guide holes in each instance extend at generally right angles to the length of the guide limb or lateral attachment limb so as to direct a drill or other surgical tool in a direction at generally right angles to the direction in which an associated quadriceps tendon (14) and patellar tendon (15) extend. The upper hole of the pair of guide holes is spaced from the superior pole of the patella in use by a distance that is typically of the order of 8 to 12 mm and commonly about 10 mm. The lower guide hole is spaced from the upper guide hole by a distance in the range of from 10 to 18 mm and typically 12 to 15 mm and especially either 12 or 15 mm depending on requirements and depending on the physical size and configuration of the relevant patella.

The surfaces or edges of the various limbs may be provided with recesses or protrusions (not shown) for cooperation with undulations of the edges of a patella.

The datum limb and guide limb mutually support an optionally removable scale panel (16) having horizontal and vertical guide lines or graduations (17) thereon for assisting a surgeon in estimating a direction at right angles to the guide limb for directing a drill or other surgical tool and also for assisting in the assessment of the depth of a hole or tunnel being formed in a patella. The scale panel is preferably transparent.

In order to accommodate different sizes of patella the accessory is made to be adjustable according to the length and breadth of the patella. The lateral attachment limb can be selectively fitted into one of a series of receiving recesses (18) in the datum limb and the transverse attachment limb may be selectively fitted into an appropriate receiving recess (19) in each of the guide limbs and lateral attachment limbs. In fitting the accessory to a patella, the datum limb should engage the superior pole (21) of the patella; the side edge of the patella should engage the guide limb and each of the lateral and transverse attachment limbs should engage the patella opposite their cooperating datum or guide limbs with the transverse attachment limb engaging the inferior pole or apex (8) of the patella.

The accessory is aimed at being located on top of the knee in the operative position, over the skin such that it forms a tight grip around the patella with protrusions (not shown) that may be of a needle like diameter to engage the skin and hold the patella without making any significant impression on the skin. The datum limb and guide limb form proximal and medial walls of the accessory and are fixed relative to each other whereas the lateral and transverse attachment limbs form distal and the lateral walls that are adjustable as per the size of a patella.

The only way that the anterior surface of the patella can be seen is through the transparent scale panel on the top of the accessory. Since the scale panel is radio-translucent, a drill bit, for example, may be visualized.

Figure 3:
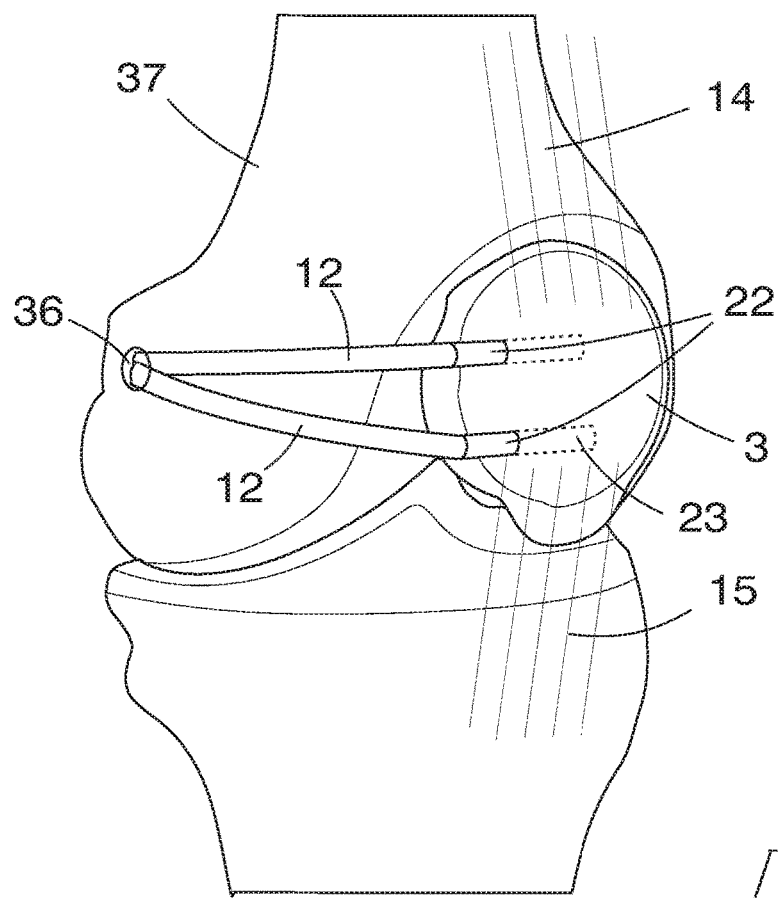
FIG. 3 is a schematic illustration of a knee joint showing one form of installed medial patella femoral ligament replacement in position.
Figure 4:
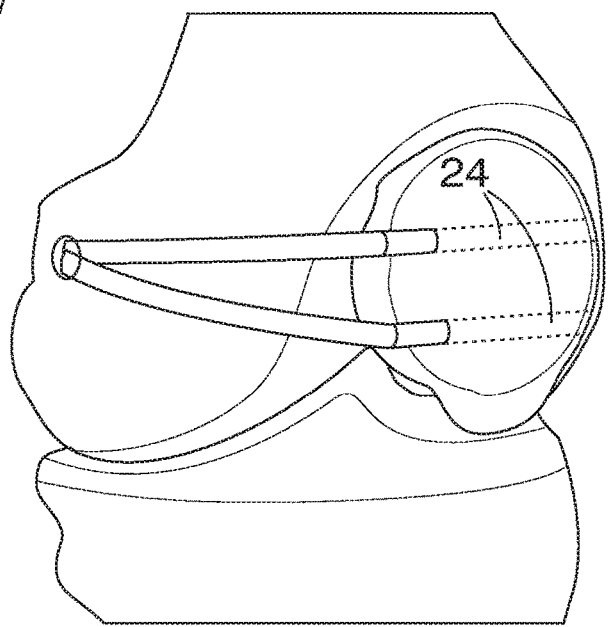
FIG. 4 is a similar schematic illustration of a knee joint showing a different form of installed medial patella femoral ligament replacement in position.
Figure 5:
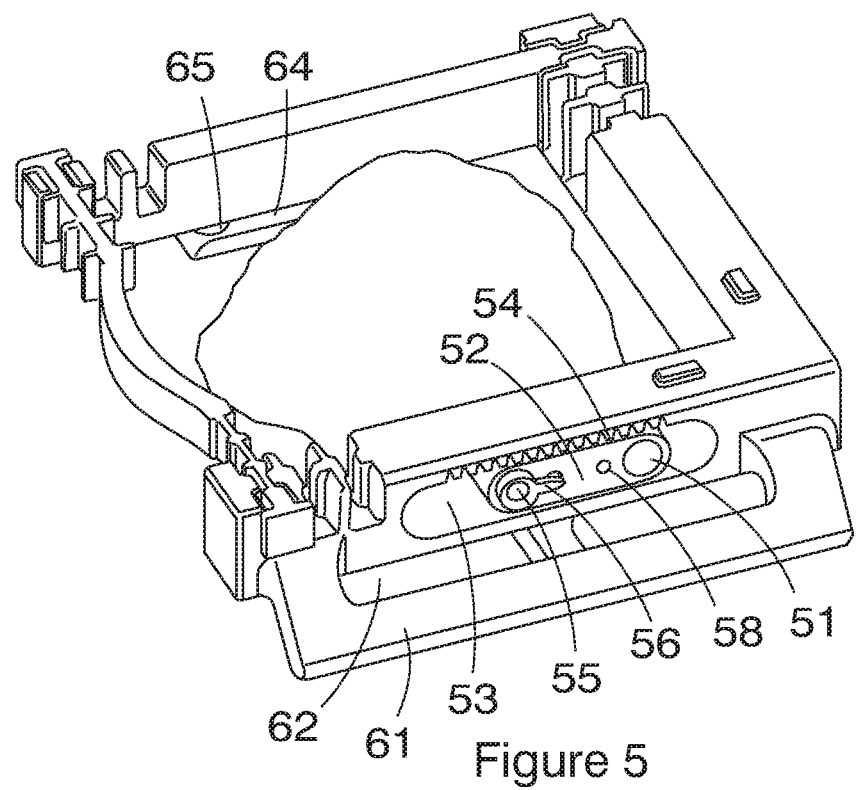
FIG. 5 is a three-dimensional illustration of a more sophisticated embodiment of the invention without a scale panel.

FIG. 3 illustrates a situation in which the attachments (22) to the patella are to blind holes (23) in the patella, and FIG. 4 illustrates the situation in which tunnels (24) pass through the patella to enable an attachment cord to be looped through the two parallel tunnels.

The basic shape and configuration of the embodiment of accessory described above may be enhanced in a number of respects that are illustrated in FIGS. 5 to 8 of the drawings.

Thus there may be provided guide holes (51) in an insert (52) received in an elongate oval recess (53) in the outer side of the guide limb. The insert has along one edge thereof formations (not visible in the drawings) co-operating with a series of co-operating integral teeth (54) extending along one longitudinal edge of the recess. The position of the holes may therefore be selected according to the prevailing size and configuration of a patella to be treated. The position of the insert will thus be one of a plurality of different positions along a part of the length of the guide limb.

The insert preferably has two holes of the same larger diameter, say 4.5 mm diameter, and at least one of which may receive a removable sleeve (55) having a bore of a smaller diameter, say 2.5 mm. An optionally smaller alternative diameter hole through the insert may thus be provided. Rotation of the sleeve within the larger diameter hole is inhibited by an integral arm (56) having a projection that clips into an aperture (58) in the insert.

The guide limb further has an integral anchor bar (61) defining, with the guide limb itself, two longitudinally juxtaposed slots (62) for receiving straps (63) passing around the anchor bar. An opposite attachment limb has a similar integral bar (64) defining a slot (65) for receiving a strap cooperating with those associated with the guide limb. The strap or straps may be made of a suitable webbing to which is attached fastening means in the form of co-operating hook and loop fastener components such as those sold under the trade name VELCRO™/Medical Tapes.

Figure 6:
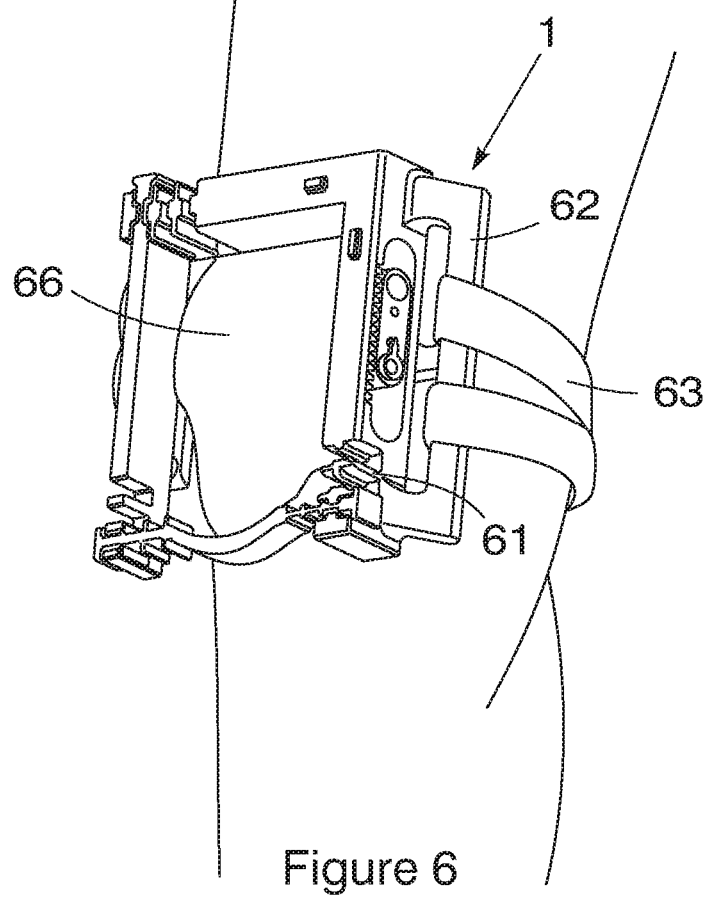
FIG. 6 is a three-dimensional view of a knee to which an accessory as illustrated in FIG. 5 has been fitted.
Figure 7:
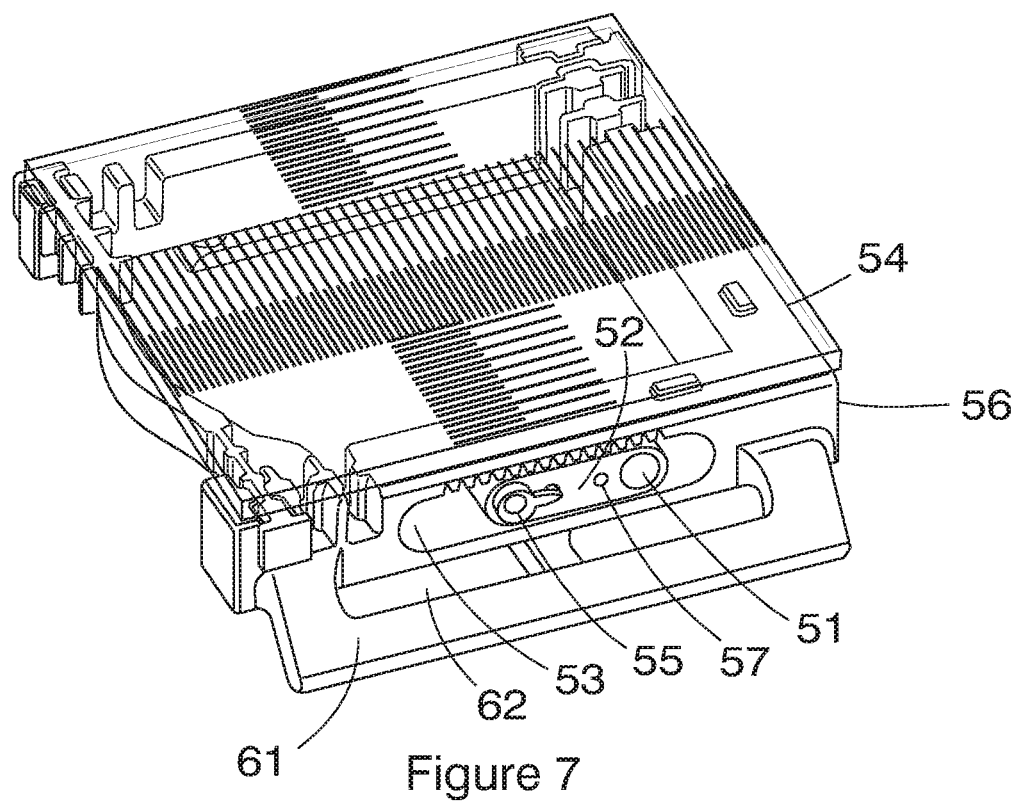
FIG. 7 is a three-dimensional view of an embodiment of the invention as illustrated in FIG. 5 from the side thereof on which the guide limb is located with a scale panel attached thereto
Figure 8:
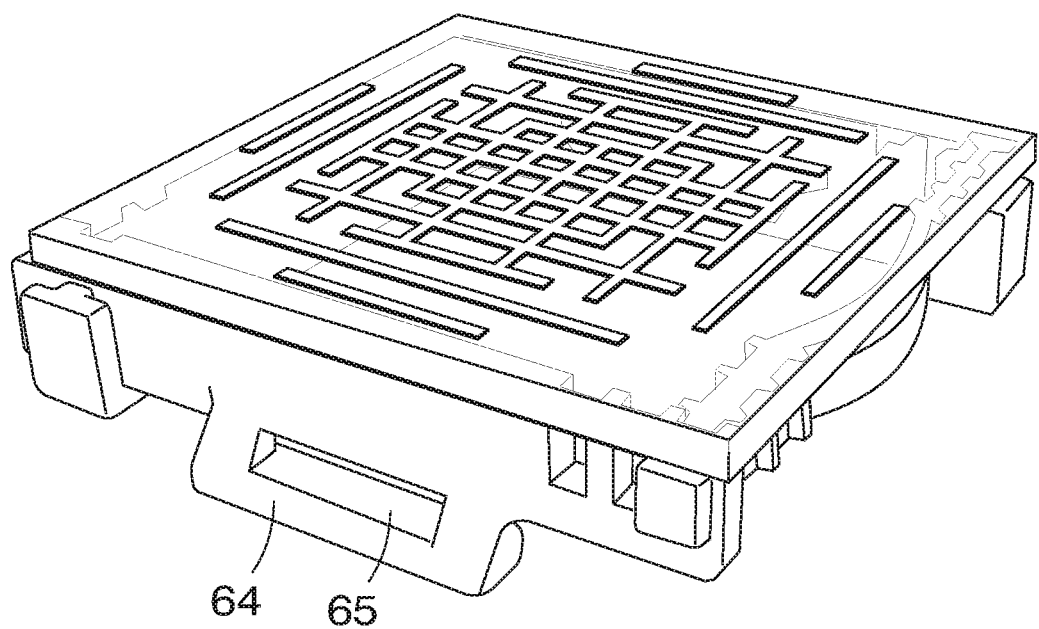
FIG. 8 is a three dimensional view of an embodiment of the invention as illustrated in FIG. 5 from the side thereof opposite of the guide limb and showing an alternative scale panel in place thereon.

FIG. 6 illustrates the enhanced accessory attached to a knee (66) of a patient by means of such straps.

A further embodiment of the invention is illustrated in FIG. 9 in which a basically U-shaped body provides a datum limb (31) forming the web of the U and a pair of generally identical guide limbs (32) extending at right angles from the datum limb. The lateral attachment limb is thus a mirror image of the guide limb and each of them may be telescopically extensible.

FIG. 9 also illustrates the provision of flexible indicator (33) extending from the one guide limb in a direction towards the femur in use, the indicator being transparent and having a guideline (34) indicating the general direction in which reconstructive ligaments (12) (see FIG. 3) should extend in the final reconstruction towards an attachment point (36) in the femur (37). The guideline will then indicate to a surgeon the general line in which reconstructive ligaments should extend and thereby indicate the line along which the attachment point to the femur should be located to avoid difficulties consequent on an incorrect direction that can result from erroneous attachment positions. This indicator assists in determining the point between the adductor tubercle and medial epicondyle of the femur to which it is desired to make the attachment.

Many other physical shapes and configurations of the attachment limbs are possible within the scope of the invention.

Thus, in another variation of the invention that is illustrated in FIG. 10, a single attachment limb (41) may be relatively flexible and attached to the datum limb (42) and the guide limb (43) by selective cooperation of formations (44, 45) that result in a variation of the effective length of the attachment limb.

FIG. 11 illustrates a further variation of the invention in which two flexible attachment limbs (46) are secured to the datum limb (47) and the guide limb (48) respectively and are adjustably joined by a releasable one-way catch or buckle mechanism (49) so that they flex to embrace the patella and urge it into contact with the datum limb and the guide limb.

Figure 12:
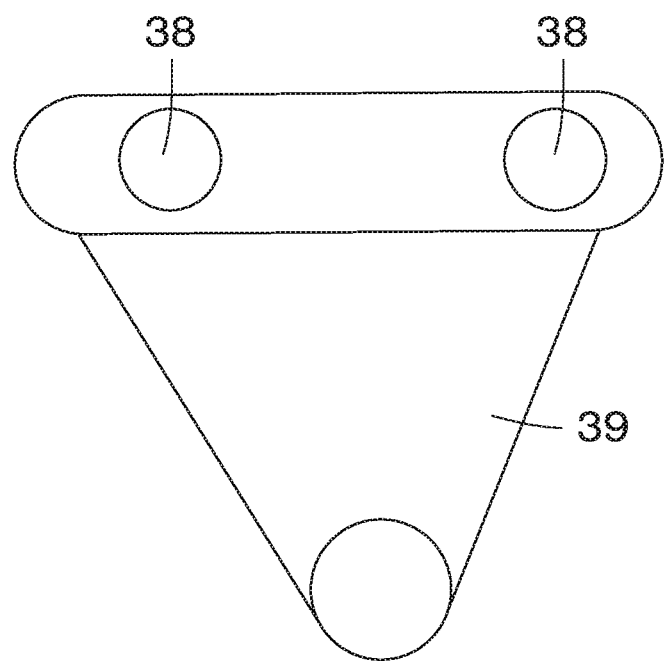
FIG. 12 shows in elevation a femoral landmark identifier that can be used to identify the femoral landmark/insertion point of a medial patella femoral ligament.

FIG. 12 shows in elevation a femoral landmark identifier (38) which is a slide system that has projections (39) that can fit in the drill holes and can be used to identify the femoral landmark/insertion point of a medial patella femoral ligament. To give a perspective, the drill guidance would assist in identifying the two drill holes indicated by the numeral (22) in FIG. 3. The femoral landmark identifier would assist in identifying the point indicated by numeral (36) in FIG. 3. The concept is that a new point (22) would be determined by the drill guide and it is thus necessary to have the femoral landmark identifier positioned with respect to the new double bundle insertion point made using the accessory of this invention.

Use of the accessory provided by the invention enables the exact medial patella femoral ligament footprint of any patient including an obese patient and a small knee of a tiny patient to be accommodated. The accessory provided by this invention enables a surgeon to locate the surgical insertion site/footprint in medial patella femoral ligament reconstruction surgeries; the proper identification of the patella medial patella femoral ligament tunnel, which is a biomechanically significant aspect to reduce possible patellar structural failure; and the parallel tunnels in the patella itself.

The accessory can be 3D printed and can therefore be made patient specific. The usage of the accessory will assist a surgeon in taking an educated decision whilst performing the surgery; the accessory can be used as a disposable surgical assist device. The same device can be used for both left and right knees.

Moreover, the accessory can reduce the number of intra-op surgical X-rays that are taken during a medial patella femoral ligament procedure.

The accessory is thus a surgical tool that can help an orthopaedic or sports surgeon to determine the exact footprint of the medial patella-femoral ligament at the patella side for the treatment of patella dislocation. It is suitable for use by all the surgeons whether they be a beginner or experienced to guide them to the exact attachment of the medial patella femoral ligament at the patella. It is anticipated that the accessory may reduce a surgeon's apprehensiveness to drill tunnels and also reduce their exposure to intra operative radiation.

Throughout the specification and claims unless the content requires otherwise the word 'comprise' or variations such as 'comprises' or 'comprising' will be understood to imply the inclusion of a stated integer or group of integers but not the exclusion of any other integer or group of integers.

The invention claimed is:

1. An accessory for use in the conduct of patella reconstruction surgery, the accessory comprising:
    an elongate datum limb for abutment in use with the superior pole of a patella optionally through the skin,
    an elongate guide limb extending transversely relative to the datum limb for abutment with a side edge of a patella such that the accessory can engage both the superior pole and side edge of a patellae simultaneously in use, and
    one or more attachment limbs for enabling the accessory to be secured in an operative position relative to a patella, and
    guide holes passing transversely through the guide limb at positions selected to direct a drill at an edge region of the patella to enable holes or tunnels to be formed in the patella at least at two required spaced positions for the attachment or reception of reconstructive ligaments to the patella,
    wherein the guide holes are provided in an insert received in a recess in the guide limb in a selected one of a plurality of different positions along a part of the length of the guide limb.

2. The accessory as claimed in claim 1 in which the guide limb is fixed relative to the datum limb at right angles to the datum limb.

3. The accessory as claimed in claim 1, wherein two spaced parallel guide holes extend at generally right angles to the length of the guide limb so as to direct a drill or other surgical tool in a direction at generally right angles to the direction in which an associated quadriceps tendon and patellar tendon extend.

4. The accessory as claimed in claim 3, wherein:
    an upper hole is spaced from the top of the patella by a distance of the order of 8 to 12 mm; and
    a lower guide hole is spaced from the upper guide hole by a distance in the range of from 10 to 18 mm.

5. The accessory as claimed in claim 1 wherein the insert has along one edge thereof formations co-operating with a series of co-operating formations in the form of an integral toothed arrangement extending along one longitudinal edge of the recess.

6. The accessory as claimed in claim 1 wherein the insert has two holes of the same diameter one or both of which may receive a removable sleeve for providing an alternative smaller diameter hole through the insert.

7. The accessory as claimed in claim 1 in which the guide limb has an integral anchor bar defining with the guide limb itself at least one longitudinally extending slot for receiving a strap or straps passing around the anchor bar with an opposite attachment limb having a similar integral bar defining a slot for receiving a belt cooperating with that associated with the guide limb.

8. The accessory as claimed in claim 1 wherein the datum limb and guide limb mutually support a scale panel having guide lines or graduations thereon for assisting a surgeon in estimating a direction at right angles to the guide limb for one or both of: (i) directing a drill or other surgical tool or (ii) assisting in the assessment of the depth of a hole or tunnel being formed in a patella.

9. The accessory as claimed in claim 1, wherein an optionally flexible indicator extends from the guide limb in a direction indicating the direction in which reconstructive ligaments should extend in a final reconstruction towards an attachment point in the femur.

10. The accessory as claimed in claim 1, wherein the one or more attachment limbs comprises a lateral attachment limb that is spaced from, and extends generally parallel to, the guide limb and a transverse attachment limb that is spaced from, and extends generally parallel to, the datum limb.

11. The accessory as claimed in claim 10, wherein the lateral attachment limb and transverse attachment limb are each adjustable in positions relative to the datum limb and guide limb so as to form generally rectangular apertures of different sizes in which a particular size of patella can be located.

12. The accessory as claimed in claim 11, wherein the lateral attachment limb serves as an alternative guide limb and has guide holes for guiding a drill or other surgical tool extending transversely to the patella.

13. The accessory as claimed in claim 10, wherein the transverse attachment limb has a downwardly curved shape in at least a central region to accommodate a lowermost apex of a patella.

14. The accessory as claimed in claim 1 wherein the accessory is made as a disposable item.

* * * * *